United States Patent
Harvey et al.

(10) Patent No.: US 8,975,463 B1
(45) Date of Patent: *Mar. 10, 2015

(54) EFFICIENT CONVERSION OF PURE AND MIXED TERPENE FEEDSTOCKS TO HIGH DENSITY FUELS

(75) Inventors: Benjamin G. Harvey, Ridgecrest, CA (US); Heather A. Meylemans, Ridgecrest, CA (US); Roxanne L. Quintana, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 43 days.

This patent is subject to a terminal disclaimer.

(21) Appl. No.: 13/605,436

(22) Filed: Sep. 6, 2012

Related U.S. Application Data

(63) Continuation-in-part of application No. 12/550,973, filed on Aug. 31, 2009, now Pat. No. 8,227,651.

(60) Provisional application No. 61/531,956, filed on Sep. 7, 2011.

(51) Int. Cl.
*C07C 403/00* (2006.01)
*C07C 403/02* (2006.01)

(52) U.S. Cl.
USPC ........................................................ 585/362

(58) Field of Classification Search
None
See application file for complete search history.

(56) References Cited

U.S. PATENT DOCUMENTS

| | | | |
|---|---|---|---|
| 4,052,549 A | 10/1977 | Booth | |
| 4,165,301 A | 8/1979 | Wiegers et al. | |
| 4,485,008 A | 11/1984 | Maa et al. | |
| 4,922,047 A | 5/1990 | Chen et al. | |
| 5,723,709 A | 3/1998 | Phillips, Jr. et al. | |
| 5,762,696 A | 6/1998 | Jordan | |
| 5,847,247 A | 12/1998 | Conte et al. | |
| 6,566,570 B1 | 5/2003 | Bergstrom et al. | |
| 6,828,283 B2 | 12/2004 | Chapaton et al. | |
| 8,227,651 B1 | 7/2012 | Harvey et al. | |

OTHER PUBLICATIONS

Meylemans, et al, Efficient conversion of pure and mixed terpene feedstocks to high density fuels. Fuel 97, (2012) 560-568.
Harvey, et al. High-Density Renewable Fuels Based on the Selective Dimerization of Pinenes, Energy Fuels 2010, 24, 267-273.

*Primary Examiner* — Tam M Nguyen
(74) *Attorney, Agent, or Firm* — Charlene A. Haley

(57) ABSTRACT

A process for making high density fuels from mixed terpene feedstocks and the resulting high density fuel products.

16 Claims, 3 Drawing Sheets

EFFICIENT CONVERSION OF PURE AND MIXED TERPENE FEEDSTOCKS TO HIGH DENSITY FUELS

CROSS-REFERENCE TO RELATED APPLICATIONS

This is a non-provisional application, claiming the benefit of, parent application Ser. No. 61/531,956 filed on Sep. 7, 2011 and is a continuation-in-part, claiming the benefit of, parent application Ser. No. 12/550,973 filed on Aug. 31, 2009 which issued as U.S. Pat. No. 8,227,651 on Jul. 24, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to a process for making a high density fuel and the resulting high density fuel product, and more specifically the dimerization of pure camphene, α-pinene, limonene, turpentine, and various mixtures of these terpenes with heterogeneous acidic catalysts.

Figure 1:
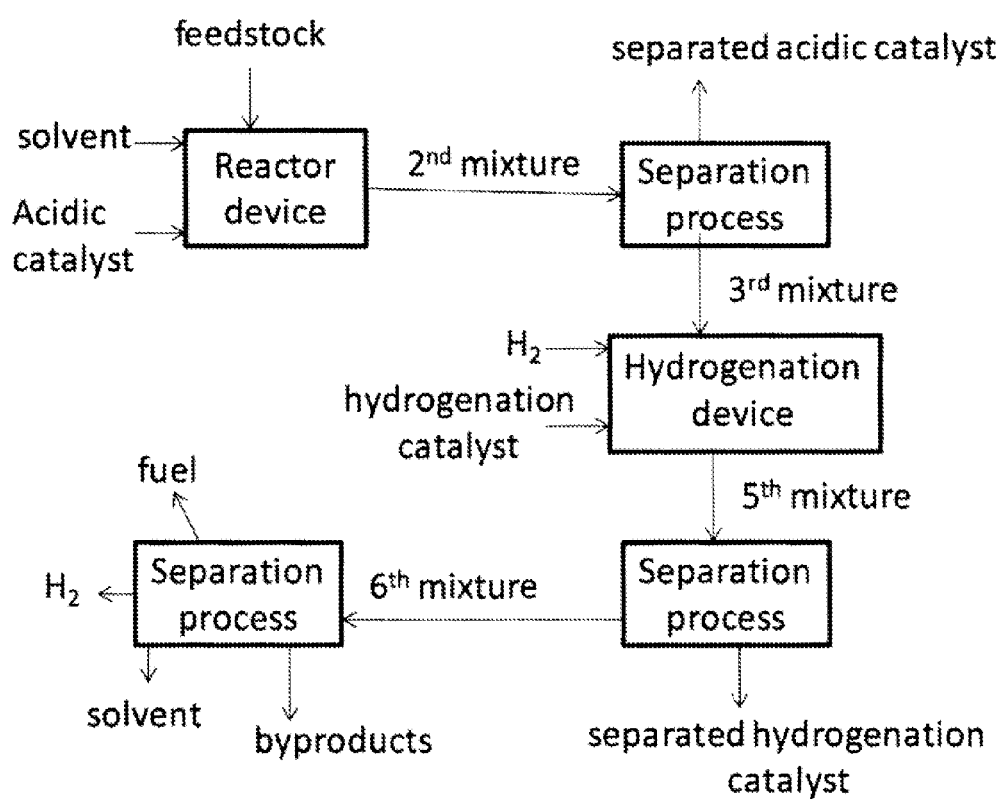
FIG. 1 is a process flow diagram for converting terpene feedstocks into high-density fuels, according to embodiments of the invention.

It is to be understood that the foregoing and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to a process for making a high density fuel and the resulting high density fuel product.

As technology and the ability to effectively utilize recalcitrant biomass sources as feedstocks for conversion to renewable fuels has improved, corresponding improvements that meet the required standard set by petroleum fuels have not been forthcoming. Feedstocks are inherently complex, oxygenated compounds. Simple, low-energy methods can be effective in producing biofuels, but those methods generally result in highly oxygenated, low-value fuels. In contrast, high temperature catalytic methods and copious amounts of hydrogen can produce high-value saturated hydrocarbon fuels, but the extra processing greatly reduces the benefit/cost ratio of using the renewable fuel.

A more elegant route to full-performance fuels lies in a biosynthetic approach in which engineered organisms convert cellulose and hemicellulose-derived sugar solutions into pure hydrocarbon products. In this manner, full performance and even ultra-performance renewable fuels can be synthesized.

Jet fuels have demanding specifications that allow for full performance under a variety of conditions. In the case of both commercial (Jet-A) and military jet fuels (JP-5 and JP-8), these specifications include constraints on the energy content, flashpoint, low temperature viscosity, and density. The ability to meet low temperature viscosity requirements while increasing the density is a difficult challenge because high molecular weight, straight chain alkanes with adequate densities also have unacceptably high melting points. For petroleum derived fuels, aromatic and other cyclic hydrocarbons effectively increase the fuel density with only a modest loss in gravimetric energy density. In contrast, most alternative fuels must be blended with petroleum derived jet fuels to meet the density requirements. In addition to jet fuels, specialty military fuels for missile propulsion have even more demanding density requirements. An example of such a specialty fuel is JP-10 (composed almost exclusively of exotetrahydrodicyclopentadiene) which has a density of 0.94 g/ml, and a net heat of combustion (NHOC) of 141,500 btu/gal. These standards cannot be met by current renewables and require specialized fuel mixtures. To address the need for full-performance renewable fuels, C10 terpenes have been investigated as precursors to renewable high density fuels (terpene dimers)

Terpenes such as α-pinene, β-pinene, camphene, and limonene are significant components of pine resin and are currently produced on an industrial scale either nondestructively by tapping trees (gum turpentine), or as a byproduct of paper pulping (crude sulfate turpentine, CST). These molecules are also promising candidates for production via biosynthetic routes as they are derived from the ubiquitous natural building block, isoprene. The ability to produce terpenes from simple sugars via cellulose presents a compelling, renewable route to the production of high performance fuels from low-value, abundant waste materials.

The synthesis of complex high density fuel mixtures produced by the heterogeneous, acid-catalyzed dimerization of β-pinene have been reported ("High-Density Renewable Fuels Based on the Selective Dimerization of Pinenes." Benjamin G. Harvey. Michael E. Wright, Roxanne L. Quintana, *Energy Fuels* 2010, 24, 267-273). The resulting fuel mixture had a volumetric energy density comparable to the tactical fuel JP-10 (141,500 btu/gal). This significant increase in gravimetric energy density over typical renewable fuels is an important consideration for tactical military platforms. Such renewable fuels could be added to jet fuel to meet density specifications, or could be used as high performance diesel fuels.

The distribution of isomers present prior to the catalytic dimerization of terpenes is an important consideration in the synthesis of high density fuels. For example, camphene and limonene are expected to reduce the volumetric net heat of combustion (NHOC) for the product fuels due to both diminished ring strain and the lower density of the molecules compared to α- and β-pinene. Properties of monomeric terpenes are compared in Table 1.

Embodiments of the invention generally relate to a process for making terpene dimers including, dimerizing at least one terpene feedstock by mixing at least one terpene with at least one heterogeneous acidic catalyst for a desired time and temperature to produce a crude terpene dimer ($C_{20}H_{32}$) mixture, hydrogenating the crude terpene dimer ($C_{20}H_{32}$) mixture with at least one hydrogenation catalyst under a hydrogen atmosphere, removing the hydrogenating catalyst(s) to produce a hydrogenated terpene dimer mixture, and utilizing a separation method against the hydrogenated terpene dimer mixture to produce substantially pure terpene dimers (high density fuel) and byproducts.

In embodiments, the feedstock is selected from the group consisting of at least one of α-pinene, β-pinene, camphene, fenchene, carene, limonene, tricyclene, and turpentine, or any combination thereof. Embodiments further include adding at least one solvent when at least one terpene feedstock is α-pinene, β-pinene, camphene, fenchene, limonene, tricyclene, turpentine, or any combination thereof and removing the solvent by distillation after the hydrogenation process is complete. In other embodiments, the solvent is selected from the group consisting of at least one of n-heptane, n-octane, other linear alkanes, 2-ethylhexane, other branched alkanes, cyclohexane, methylcyclohexane, other cycloalkanes, other non-aromatic liquid hydrocarbons, and any combination thereof.

In embodiments, the acid catalyst is selected from the group consisting of at least one of perfluorinated sulfonic acid resin, polyacidic clay, sulfonated polystyrene resin, mesoporous zeolites. Nation, MMT-K10, and any combination thereof. Embodiments further include a dimerizing step for a time period selected from the range of 0.5 to about 24 hours and at the temperature selected from the range of about 0° to about 160° C. In embodiments, the separation method or removing method is selected from at least one of filtration, decantation, distillation and centrifugation. In embodiments, the hydrogenation catalyst having Ni, Pd, Pt, or Cu, including platinum oxide, palladium oxide, platinum supported on carbon, palladium supported on carbon, porous metallic nickel, and any combination thereof. In embodiments, overpressure is in the range of about 1 pound to about 750 pounds per square inch.

In embodiments, the byproducts include at least one of p-cymene and organic reaction products having greater than 20 carbon atoms. In other embodiments, the hydrogenated mixture includes about 50 to about 95% hydrogenated terpene dimers and about 1 to about 15% said hydrogenated terpene trimers. In embodiments, the high density fuel includes >90% hydrogenated terpene dimers. In embodiments, the fuel has a density in the range of 0.90 to about 0.95 grams per cubic centimeter and a NHOC (heat of combustion) in the range of 135,000 to about 145,000 btu/gallon measured at Standard Temperature and Pressure. Embodiments further include adding to the fuel about 10 to about 90% by volume from the group consisting of at least one of, JP-4, JP-5, JP-8, JP-10, F-76, RJ-4, hydrogenated pinene monomers, diesel fuels, fuels from renewable or alternative sources, and any combination thereof to produce a blended fuel. Other embodiments further include substantially isolating at least one of the byproducts including p-cymene, heavy oligomers (trimer, tetramer), and hydrogenated monomers. In embodiments of the invention the process is continuous. In embodiments, the process is conducted with the terpenes in the gas phase. Another aspect of the invention includes the fuels and/or pure terpene dimers produced by the processes and methods herein.

TABLE 1

Selected properties of monomer terpenes

| property | β-pinene | α-pinene | limonene | camphene |
|---|---|---|---|---|
| Density (g/mL) | 0.859 | 0.858 | 0.841 | 0.842 |
| $\Delta H_f(l)$ (kJ/mol) | −7.7 | −16.4 | −50.8 | −66 |
| $\Delta H_f(g)$ (kJ/mol) | 35.8 | 30.2 | −12.2 | −28 |

Considering that the heats of combustion of the terpene monomers are ~6000 kJ/mole, the subtle differences in the heats of formation of the monomer terpenes (Table 1) indicate that ring strain is only a minor contributor to the improved net heats of combustion of the dimers (~1% increase). In contrast, the significantly higher density of the dimers (up to about 10% higher) is the key factor in improving volumetric net heats of combustion.

β-Pinene is an interesting feedstock component due to the ease of dimerization allowed by its exocyclic double bond. However, β-pinene is subject to isomerization prior to dimerization. The main isomeric products are α-pinene, limonene, and camphene (Scheme 1). Camphene is the most difficult isomer to dimerize and requires highly acidic catalysts to fully convert it to dimers.

Scheme 1. Productions of the isomerization of β-pinene

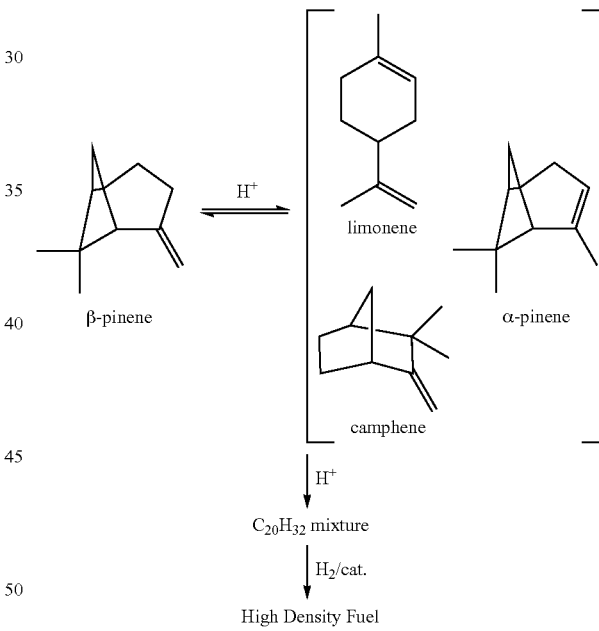

Other factors including the structure of the product dimers, the propensity for monomers to cross-couple, and the activity of different monomers with various acid catalysts can have important effects on key properties including density, freezing point, and low temperature viscosity. In particular, the low temperature viscosity of these fuels is important for determining the suitability of terpene dimers as high density tactical fuels.

Embodiments of the invention relate to the dimerization of pure camphene, α-pinene, limonene, turpentine, and various mixtures of these terpenes with heterogeneous acidic catalysts. Embodiments of the invention describe the use of low cost, unpurified feedstocks that include multiple terpenoids in variable amounts.

There are three types of reactions occurring in the overall process: (1) isomerization, (2) oligomerization (primarily dimerization), and (3) hydrogenation. Depending on the particular feedstock and reaction conditions, variable degrees of isomerization occur concurrently with the dimerization reaction. Significant amounts of isomerization of β-pinene and α-pinene occur prior to dimerization. Isomerization of these pinenes gives primarily camphene and limonene. Given that camphene is the main product of the isomerization process and does not convert to other terpenes under the reaction conditions, the final fuel mixtures derived from α-pinene and β-pinene are composed primarily of camphene dimers. Therefore, these camphene dimers largely determine the properties of the final fuel mixtures.

Limonene does not interconvert with the pinenes, but instead isomerizes to different positional isomers. Thus, the dimers derived from limonene have a lower density, as expected, because they have a less compact structure compared to the bicyclic terpenes. Also of interest is the difference in density between dimer mixtures prepared from β-pinene with Nafion as the catalyst in contrast to the mixtures prepared with MMT-K10 as the catalyst. MMT-K10 does not have strong enough acid sites to efficiently homodimerize camphene. This leads to both lower yields and a reduced density due to the higher percentage of limonene-type structures in the mixture.

An embodiment of this invention is the use of Nafion® SAC-13 and MMT-K10 as catalysts for the dimerization of α-pinene/camphene mixtures. These catalysts gave unexpectedly efficient conversions of terpenoid mixtures to terpene dimers. The known mechanisms of isomerization, dimerization, and other competitive reactions do not account for the high conversion to dimers that is observed regardless of the α-pinene/camphene ratio. At low concentrations of α-pinene one would have expected modest dimer yields.

A general process flow diagram for the dimerization of terpene feedstocks is shown in FIG. 1. The dimerization reaction, concurrent with isomerization and oligomerization reactions, is carried out in a reactor device. After completion of the dimerization reaction, the acidic catalyst is removed from the reaction mixture. The reaction mixture is placed in a hydrogenation device along with hydrogen and a hydrogenation catalyst. After the hydrogenation, the hydrogenation catalyst is removed. Then the hydrogenated mixture is refined, typically in a fractional distillation process, to provide the desired fuel. Other valuable byproducts, such as p-cymene and higher oligomers are also isolated. The higher oligomers may be used as resins, lubricants, and adhesives. FIG. 1 is a process flow diagram for converting terpene feedstocks into high-density fuels.

General Process Procedures. For the examples described below, the following laboratory procedures and methods were employed. Regarding materials, Nafion (Ion-Power Inc.) was precipitated from a 20% water/alcohol dispersion by the addition of $CH_2Cl_2$ and ether, followed by filtration and drying under vacuum (4 Torr) at ambient temperature. Montmorillonite K10 (MMT-K10) (Aldrich) and Nafion SAC-13 (Aldrich) were heated (100° C.) under vacuum (30 Torr) overnight prior to use. α-pinene, (−)-β-pinene, (R)-(+)-limonene and camphene were all purchased from Aldrich and used without further purification. Turpentine was purchased from the Home Depot, and used without further purification. Regarding the dimerization reactions, the reactor device was a 250 mL three-neck flask equipped with a reflux condenser, pressure-equalizing addition funnel, and gas inlet. The flask was agitated with a Teflon-coated stir bar. The flask was placed in an oil bath (or an ice bath) to maintain a constant temperature. Hydrogen gas produced in the reaction was vented through a mercury bubbler. The hydrogenations were performed in a Parr Series 3926 shaker hydrogenation apparatus (a glass bomb) under 40 psi of hydrogen-over-pressure. The atmosphere in the flask was exchanged with hydrogen through several evacuation/backfill cycles. After hydrogenation, the hydrogenated mixture was fractionally distilled. Product mixtures were analyzed with an Agilent 6890-GC system with a Restek RTX-5MS 30-meter column. The GC inlet temperature was 250° C. and the column oven temperature program began at 40° C. for three minutes and increased to 350° C. at 10° C./min. An Agilent mass selective detector (MSD) 5973 system was used to identity the sample's components. $^1H$ and $^{13}C$ NMR measurements were performed using a Brüker Avarice II 300 MHz spectrometer. Dimerizations of pure terpenes were periodically monitored by NMR spectroscopy prior to completion of the reaction. Herein, the methods of stirring, shaking, and other mechanical methods of moving the reaction mixture are encompassed by the term 'agitating.'

In process Examples 1-3, the use of camphene as the feedstock resulted in a negligible amount of residual monomer, while α-pinene and limonene resulted in 7 and 15% residual monomer, respectively (Table 2). The bulk of this difference is attributable to the known dehydrogenation reaction that converts limonene to p-cymene over acid catalysts. Camphene does not isomerize to limonene which allows for all of that monomer to be converted to dimer and trimer. Although the production of p-cymene reduces the overall yield of dimers, this bio-available aromatic has utility as an additive to jet fuels to swell o-rings and seals.

TABLE 2

Acid catalyzed conversion of pure terpenes to dimers

| Terpene | Catalyst | Rxn Time (h) | Monomer | Dimer | Trimer |
|---|---|---|---|---|---|
| camphene | Nafion | 2 | — | 86 | 14 |
| α-pinene | Nafion | 5 | 7 | 79 | 14 |
| limonene | Nafion SAC-13 | 2 | 15 | 85 | — |

EXAMPLE 1

Camphene Dimerization. A flask was equipped as described above. Camphene (95 grams) and Nation powder (500 mg) were placed in a flask, then 40 mL of heptane was added and the mixture was slowly heated to 100° C. The progress of the reaction was monitored by NMR spectroscopy and the reaction was complete in ~20 hours.

EXAMPLE 2

α-Pinene Dimerization. A flask was equipped as described above. Nation powder (500 mg) and 30 mL of heptane was added to the flask and the mixture was heated to 100° C. with rapid stirring. Once the heptane was refluxing, 100 mL of α-pinene was slowly added. The progress of the reaction was monitored by NMR spectroscopy, and the reaction was complete in ~18 hours.

EXAMPLE 3

Limonene Dimerization. A flask was equipped as described above. Nation SAC-13 (1.5 g) and 40 mL of heptane (40 mL) was added and the mixture heated to 100° C.

with rapid stirring. Once the mixture was refluxing, 100 mL limonene was very slowly added. The progress of the reaction was monitored by NMR spectroscopy, and the reaction was complete in 2 hours.

EXAMPLE 4

β-Pinene Dimerization. A flask was equipped as described above. MMT-K10 (2 g) and heptane (40 mL) were added to the flask and the mixture was heated to 100° C. with rapid stirring. Once the mixture was refluxing 100 mL β-pinene was very slowly added. Immediately the clay turned a red-orange color with evolution of hydrogen, which was vented through a mercury bubbler. The progress of the reaction was monitored by NMR spectroscopy, and was complete in 2 hours.

EXAMPLE 5

Figure 2:
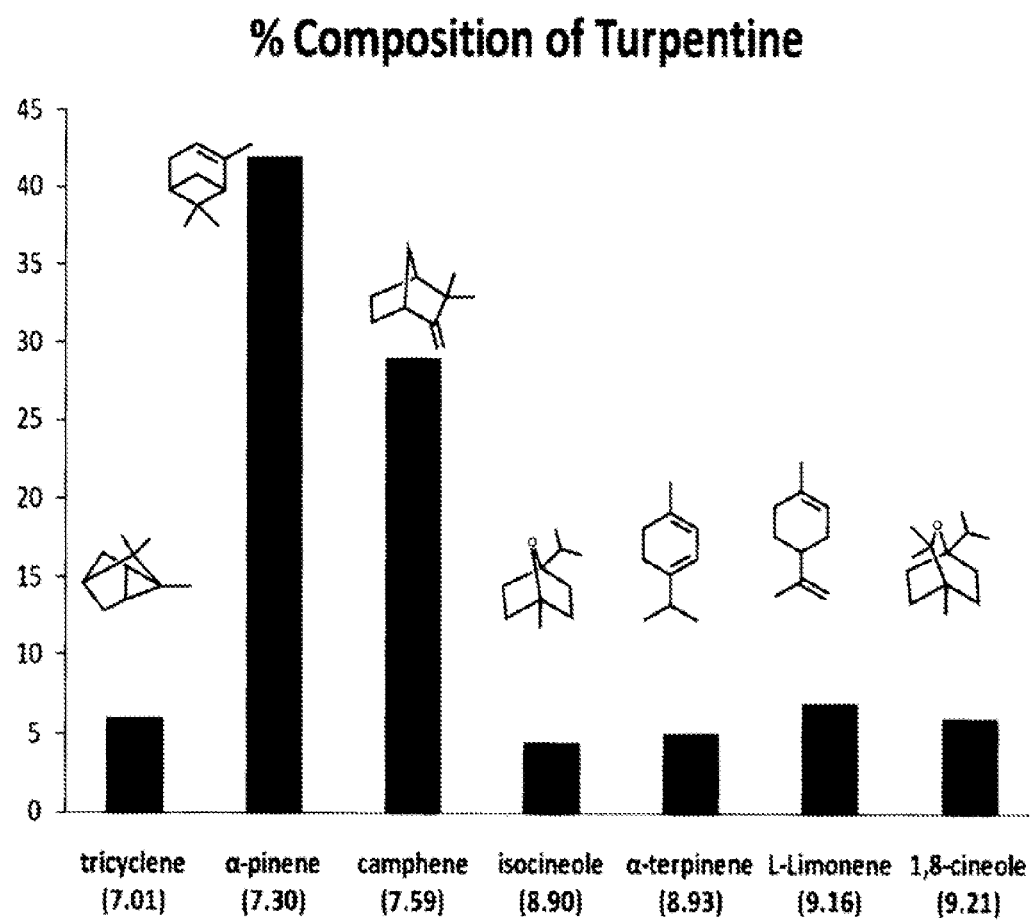
FIG. 2 is a graph of the composition of a commercial (crude) turpentine.

Composition of a crude commercial turpentine. The composition of a commercial crude turpentine was analyzed by GC-MS (FIG. 2). There was a large amount of camphene present in the crude mixture and an absence of β-pinene. FIG. 2 is a graph of the composition of a commercial grade (crude) turpentine.

EXAMPLE 6

Turpentine Dimerization. A low-grade natural turpentine (namely a crude terpene mixture derived from a simple distillation of pine resin) was tested for its suitability as a replacement for reagent grade terpenes to determine if sufficient conversion to dimer molecules could be realized. A flask was equipped as described above. As a representative example: Nation SAC-13 (5.5 g) and 150 mL of heptane were added. The mixture was heated to 100° C. with rapid stirring. Once the heptane was refluxing, 250 mL of turpentine was slowly added. The reaction was allowed to reflux under $N_2$ and progress was monitored by GC-MS. Complete reaction took ~12 hours. The results are shown in

TABLE 3

Conversion of crude turpentine to terpene dimers.

| Catalyst | Monomer (%) | Dimer (%) | Trimer (%) |
|---|---|---|---|
| MMT-K10 | 23 | 66 | 11 |
| Nafion | 29 | 70 | 1 |
| Nafion SAC-13 | 12 | 81 | 7 |

Nation SAC-13 converted the crude mixture to 81% dimer with 7% trimer formation. In similar runs, MMT-K10 produced dimer in 66% yield with 11% trimer: unsupported Nation powder gave conversion yielding 70% dimer with 1% trimer formation. The yield of dimers is particularly impressive in light of the oxygenated components, namely isocineole and 1,8-cineole that make up 10% of the crude mixture. Based on the observation that both Nation SAC-13 and MMT-K10 effectively dimerized mixtures of camphene and α-pinene despite their inability to dimerize the neat terpenes, it can be assumed that a synergistic process between terpene monomers was occurring in the reaction. The solid acid catalysts of this invention effectively dimerized these low-value mixtures to produce a specialized high density fuel, thus obviating the need for initial purification.

EXAMPLE 7

Dimerization of Camphene/α-Pinene Mixtures. A flask was equipped as described above. Either 150 mg of Nation SAC-13 or 300 mg of MMT-K10 and 10 mL of heptane were added and the mixture was heated to 100° C. with rapid stirring. Mixtures with varying concentrations of camphene and α-pinene (10 g total) were prepared. The camphene was allowed to fully dissolve in the α-pinene before addition to the reaction flask. Once the heptane was refluxing the mixture was slowly added. The reaction was allowed to reflux under $N_2$ for 13 hours and the product was then analyzed by GC-MS. For Nafion SAC-13, when the volume ratio of α-pinene to camphene was changed from 70:30 to 30:70, conversion to dimer remained high, with an average of 87% dimer and only 3% trimer, MMT-K10 behaved in a similar fashion with an average conversion to dimer of 57% with 10% trimer (Table 4). To assess if limonene had any effect on the product distribution, 10% (by volume) limonene was added to an MMT-K10 catalyzed reaction. A subtle decrease in the amount of trimer produced was observed, along with an increase in residual monomer.

TABLE 4

Conversion of mixed a-pinene/camphene to dimers.

| Catalyst | α-pinene:camphene | Monomer (%) | Dimer (%) | Trimer (%) |
|---|---|---|---|---|
| MMT-K10 | 70:30 | 32 | 57 | 11 |
| MMT-K10 | 60:40 | 32 | 58 | 10 |
| MMT-K10 | 50:40 (10% limonene added) | 37 | 57 | 6 |
| MMT-K10 | 40:60 | 34 | 56 | 10 |
| Nafion SAC-13 | 70:30 | 10 | 84 | 6 |
| Nafion SAC-13 | 60:40 | 12 | 88 | — |
| Nafion SAC-13 | 50:50 | 12 | 87 | 1 |
| Nafion SAC-13 | 30:70 | 6 | 89 | 5 |

EXAMPLE 8

Dimer Hydrogenation/Purification. The crude dimer mixtures form the reactions outlined above were all hydrogenated using a Parr hydrogenation apparatus (the hydrogenation device in FIG. 1). The crude mixtures were filtered to remove all of the catalyst, and transferred into a glass bomb. To each mixture, an appropriate amount of $PtO_2$ or Pd/C was added. The mixture was then placed in the apparatus and the glass bomb was evacuated and backfilled with hydrogen. This was repeated several times to create a hydrogen atmosphere at a hydrogen overpressure of 30-40 psi. The reaction was shaken at this pressure until hydrogen uptake ceased and the saturation of the alkenes was confirmed by NMR spectroscopy. The reaction time for these experiments was between 2-5 hours. The reaction mixture was then filtered through a plug of Celite® to remove the catalyst and the filtrate was fractionally distilled under reduced pressure. The dimer fraction was collected from 118-140° C. at 0.5 Torr.

EXAMPLE 9

The volumetric net heat of combustion and density of the dimer mixtures is affected by the choice of starting monomeric feedstock. The NHOC varies from a maximum of 142,013 btu/gal for camphene dimers to 137,423 btu/gal for limonene dimers (Table 5).

TABLE 5

Net Heat of Combustion of Terpene Dimer Fuels

| Monomer | NHOC (MJ/Kg) | C (%) | H (%) | Density (g) | NHOC (btu/gal) |
|---|---|---|---|---|---|
| camphene | 42.063 | 87.66 | 11.75 | 0.941 | 142013 |
| α-pinene | 42.047 | 87.55 | 11.87 | 0.935 | 141054 |
| β-pinene | 42.118 | 87.72 | 12.12 | 0.938 | 141745 |
| Limonene | 41.906 | 87.35 | 12.21 | 0.914 | 137423 |
| β-pinene (clay) | 41.978 | 87.35 | 11.97 | 0.932 | 140370 |

The gravimetric net heat of combustion was similar regardless of the monomer(s) used (~42 MJ/kg). Therefore, the volumetric net heat of combustion is primarily a function of the density of the mixture. All of the terpene dimer fuel mixtures have NHOCs and densities comparable to JP-10 and far higher than petroleum derived gasoline, JP-5, and diesel fuel.

As a comparison, biodiesel, considered to be an exceptionally dense renewable fuel, has only 83% of the NHOC of camphene dimers (Table 6).

TABLE 6

Net heat of combustion, density, and freezing point of various fuels.

| Fuel | Net Heat of Combustion (MJ/L) | Net Heat of Combustion (btu/gal) | Density (g/cc) | Freezing Point or Pour Point (PP) degrees K |
|---|---|---|---|---|
| JP-5 | 34.8 | 125,000 | 0.82 | <227 |
| JP-10 | 39.6 | 142,000 | 0.94 | <194 |
| RJ-5 | 44.9 | 161,000 | 1.08 | >255 |
| Gasoline | 32.3 | 115,900 | 0.74 | <173 |
| Diesel No. 2 | 36.0 | 129,000 | 0.85 | 261-267 (PP) |
| Biodiesel | 32.9 | 118,000 | 0.88 | >263 (PP) |
| β-pinene | 36.9 | 132,500 | 0.86 | 212 |
| α-pinene | 36.9 | 132,300 | 0.86 | 209 |

EXAMPLE 10

The viscosities of the mixtures. A study was conducted to determine the effect of starting monomer on the viscosity of the resulting dimer mixture (Table 7). The viscosities of these fuels were measured at 40° C. so that the results would not be affected by proximity to the freezing points of various compounds in the mixtures.

TABLE 7

Viscosity of Terpene Dimer Fuels

| Monomer | Viscosity (40° C., cSt) |
|---|---|
| camphene | 34.96 |
| α-pinene | 34.68 |
| β-pinene | 35.05 |
| limonene | 25.86 |

In line with the density results, camphene appeared to exert the most influence on the viscosity of the dimer mixtures derived from α- and β-pinene. The dimers produced from all of the bicyclic terpenes had remarkably similar viscosities averaging ~35 cSt for dimers prepared from camphene, α-pinene, and β-pinene (Table 7). In contrast, limonene yielded a fluid with much lower viscosity (25.9 cSt). Based both on the density and viscosity results, it is likely that limonene forms linear dimers (Scheme 2).

Scheme 2. Example of a linear dimerization product derived from limonene.

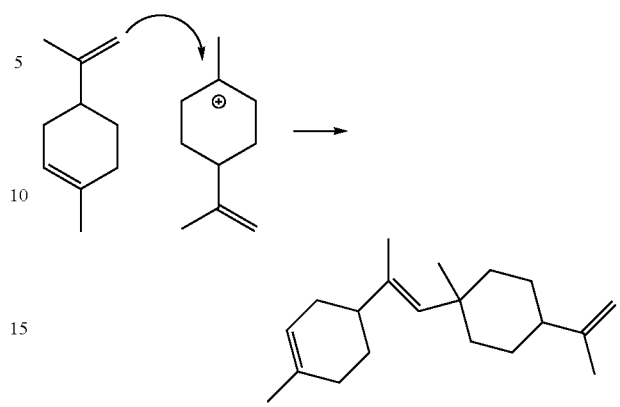

To put these viscosity numbers in perspective, it should be noted that the values measured for terpene dimer fuels are comparable to those of vegetable oils (30-50 cSt), whereas diesel fuel (1.9-4.1 cSt) and biodiesel (fatty acid methyl esters 3.5-5 cSt) have dramatically lower viscosities. Although the high viscosity of these fuels may preclude their use as standalone fuels for certain applications, mixtures with conventional or renewable fuels have been shown to reduce their viscosities for use in a wide variety of applications.

EXAMPLE 11

Figure 3:
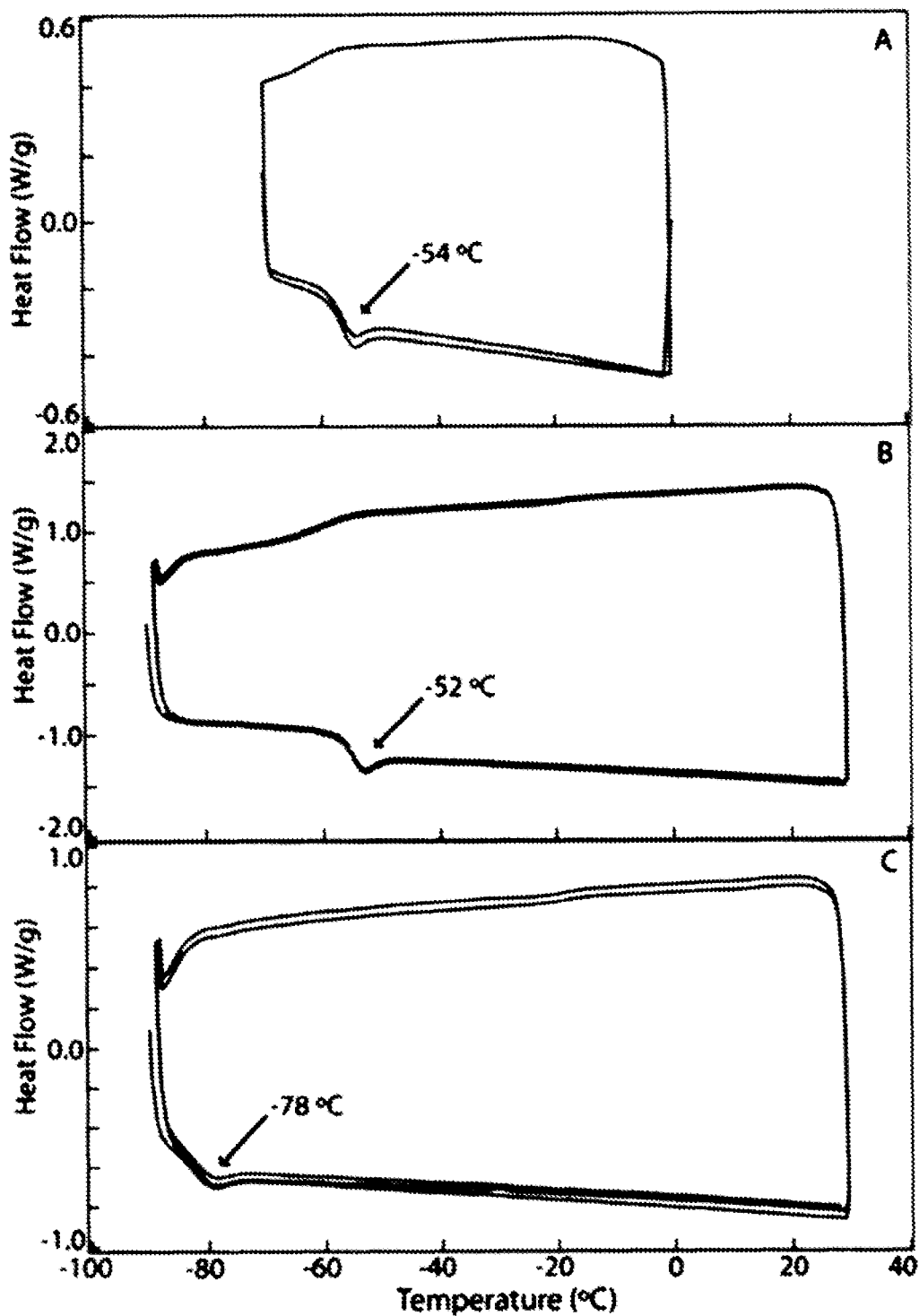
FIG. 3 is a graph illustrating DSC freezing-point data for dimers derived from camphene (A), α-pinene (B), and limonene (C), according to embodiments of the invention.

Freezing points of mixtures of terpene dimer fuels. Pinene dimers have pour points on the order of −30° C. However, there were only subtle differences in the pour points between the different mixtures listed in Table 7. Differential Scanning Calorimetry (DSC) can be utilized to explore the low temperature behavior of various fuel mixtures. In the case of petroleum based jet fuels, the heating curve is much more effective than the cooling curve in determining the melting point of various fuels. These melting points are characterized by sharp exotherms due to the high heat of fusion for normal alkanes present in solution. In the case of pinene dimers, the products are complex cycloalkanes. Straight chain alkanes can have heats of fusion up to an order of magnitude higher than simple cycloalkanes such as methylcyclopentane. Therefore, the response of the pinene dimers in the DSC is significantly less than that observed for jet fuels. However, the subtle DSC response was observable and reproducible upon subsequent cycles (FIG. 3). FIG. 3. DSC freezing-point data for dimers derived from camphene (A), α-pinene (B), and limonene (C).

The data clearly show an endotherm on the heating cycle at −54° C. for camphene dimers, −52° C. for dimers derived from α-pinene, and −78° C. for limonene dimers. The complementary exotherms on the cooling cycle are much broader and less diagnostic. In line with the conclusions derived from the density and viscosity data, it appears that camphene dimers greatly affect the freezing point of the fuel mixtures derived from the bicyclic terpenes.

EXAMPLE 11

Viscosities of Blends. Specialty fuels based on high-viscosity norbornadiene dimers, which have high melting points, can only be considered as missile fuel components in combination with a low freezing component. Likewise, pinene dimer/JP-10 blends may potentially be used as partially renewable surrogates for petroleum-based, high-density fuels, and pinene dimer/monomer mixtures as a fully renewable surrogate. To explore these possibilities, the viscosities of several mixtures of a terpene dimer fuel (synthesized from turpentine) with various jet, missile, and renewable fuels were measured (Table 8)

TABLE 8

Viscosities of Terpene Dimer Fuel Blends

| Fuel Blend | Viscosity (cp) | | |
|---|---|---|---|
| | ~10° C. | 21° C. | 30° C. |
| 100% Turpentine Dialers | 3939 | 89.2 | 46.5 |
| 50:50 JP-8 | 3.66 | 1.86 | |
| 50:50 JP-10 | 23.9 | 7.45 | 6.12 |
| 50:50 RJ-4 | 53.0 | 11.2 | 8.16 |
| 50:50 Pinane | 24.9 | 7.20 | 5.43 |

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A process for making terpene dimers, comprising:
    dimerizing at least one terpene feedstock by mixing said at least one terpene with at least one heterogeneous acidic catalyst and at least one solvent used to control the reaction temperature for a desired time and temperature to produce a crude terpene dimer ($C_{20}H_{32}$ mixture) in about 65% to about 95% chemical yield;
    hydrogenating said crude terpene dimer ($C_{20}H_{32}$ mixture) with at least one hydrogenation catalyst under a hydrogen atmosphere and removing said hydrogenating catalyst(s) to produce a about 65% by weight to about 95% by weight of hydrogenated terpene dimer mixture; and
    utilizing a separation method against said hydrogenated terpene dimer mixture to produce substantially pure terpene dimers (high density fuel) and byproducts, wherein said process generates a hydrocarbon mixture with a viscosity of between about 20 and 50 cSt at 40° C.

2. The process of claim 1, wherein said feedstock is selected from the group consisting of at least one of α-pinene, β-pinene, camphene, fenchene, carene, limonene, tricyclene, and turpentine, or any combination thereof.

3. The process of claim 1, wherein said solvent is selected from the group consisting of at least one of n-heptane, n-octane, other linear alkanes, 2-ethylhexane, other branched alkanes, methylcyclohexane, cyclic alkanes with boiling points above 90° C., other non-aromatic liquid hydrocarbons, and any combination thereof; and removing said solvent by distillation after said hydrogenation process is complete.

4. The process of claim 1, wherein said acid catalyst is selected from the group consisting of at least one of perfluorinated sulfonic acid resin, polyacidic clay, sulfonated polystyrene resin, mesoporous zeolites, Nafion, MMT-K10, and any combination thereof.

5. The process of claim 1, further comprising said dimerizing step for a time period selected from the range of 0.5 to about 24 hours and at the temperature selected from the range of about 0° to about 160° C.

6. The process of claim 1, wherein said separation method or said removal of said hydrogenating catalyst(s) is selected from at least one of filtration, decantation, distillation and centrifugation.

7. The process of claim 1, wherein said hydrogenation catalyst having Ni, Pd, Pt, or Cu, including platinum oxide, palladium oxide, platinum supported on carbon, palladium supported on carbon, porous metallic nickel, and any combination thereof.

8. The process of claim 1, wherein said hydrogen atmosphere is in the range of about 1 pound to about 750 pounds per square inch.

9. The process of claim 1, wherein said byproducts comprise at least one of p-cymene and organic reaction products having greater than 20 carbon atoms.

10. The process of claim 1, wherein said hydrogenated mixture comprises
    about 65 to about 95% said hydrogenated terpene dimers; and
    about 1 to about 15% said hydrogenated terpene trimers.

11. The process of claim 10, wherein said high density fuel comprises >90% hydrogenated terpene dimers.

12. The process of claim 11, wherein said fuel has a density in the range of 0.90 to about 0.95 grams per cubic centimeter and a NHOC (heat of combustion) in the range of 135,000 to about 145,000 btu/gallon measured at Standard Temperature and Pressure.

13. The process of claim 11, further comprising adding to said fuel about 10 to about 90% (by volume) from the group consisting of at least one of JP-4, JP-5, JP-8, JP-10, F-76, RJ-4, hydrogenated pinene monomers, diesel fuels, fuels from renewable sources, and any combination thereof to produce a blended fuel, wherein said blended fuel generates a hydrocarbon mixture with a viscosity of between about 1 and 90 cP at 21° C.

14. The process of claim 1, further comprising substantially isolating at least one of said byproducts including p-cymene, heavy oligomers (trimer, tetramer), and hydrogenated monomers.

15. The process of claim 1, wherein said process is continuous.

16. The process of claim 15, wherein said process is conducted with the terpenes in the gas phase.

* * * * *